United States Patent
Zhdanov et al.

(10) Patent No.: US 10,025,831 B2
(45) Date of Patent: Jul. 17, 2018

(54) ADAPTIVE SHORT LISTS AND ACCELERATION OF BIOMETRIC DATABASE SEARCH

(71) Applicant: BIO-key International, Inc., Eagan, MN (US)

(72) Inventors: Renat Zhdanov, Eagan, MN (US); Alexander Ouchveridze, Plymouth, MN (US)

(73) Assignee: BIO-key International, Inc., Eagan, MN (US)

( * ) Notice: Subject to any disclaimer, the term of this patent is extended or adjusted under 35 U.S.C. 154(b) by 496 days.

(21) Appl. No.: 14/677,061

(22) Filed: Apr. 2, 2015

(65) Prior Publication Data

US 2015/0331867 A1 Nov. 19, 2015

Related U.S. Application Data

(60) Provisional application No. 61/993,643, filed on May 15, 2014.

(51) Int. Cl.
*G06F 17/30* (2006.01)
*G06F 19/24* (2011.01)
*G06F 19/28* (2011.01)

(52) U.S. Cl.
CPC .... *G06F 17/3053* (2013.01); *G06F 17/30554* (2013.01); *G06F 19/24* (2013.01); *G06F 17/30* (2013.01); *G06F 19/28* (2013.01)

(58) Field of Classification Search
CPC ........... G06F 17/3053; G06F 17/30554; G06F 19/24; G06F 19/28
See application file for complete search history.

(56) References Cited

U.S. PATENT DOCUMENTS 5,841,888 A * 11/1998 Setlak ................. A61B 5/1172
382/124
6,047,281 A 4/2000 Wilson et al.
(Continued)

FOREIGN PATENT DOCUMENTS

JP 2002-229953 A 8/2002
WO WO 2009/079219 A1 6/2009

OTHER PUBLICATIONS

International Search Report and Written Opinion for International Application No. PCT/US2015/024009, dated Jun. 10, 2015, date of filing: Apr. 2, 2015, 10 pages.
(Continued)

*Primary Examiner* — Tarek Chbouki
(74) *Attorney, Agent, or Firm* — Kelly, Holt & Christenson, PLLC

(57) ABSTRACT

A system for comparing a biometric sample against a biometric dataset is provided. In one embodiment, a system for comparing a biometric sample against a biometric dataset comprises a database storing at least one biometric dataset. The system may also comprise a comparison module configured to iteratively provide a comparison score for each record in the biometric dataset, wherein the comparison score indicates a likelihood of match between an individual record in the biometric dataset and the biometric sample; wherein, during each iteration. The steps in the iteration may comprise retrieving a model of each of the plurality of records. The steps in the iteration may also comprise comparing the model of each of the plurality of records against the biometric sample. The steps in the iteration may also comprise generating the comparison score for each of the plurality of records. The steps in the iteration may also comprise iteratively compare the biometric sample against a plurality of records. The steps in the iteration may also comprise wherein the resolution of the retrieved model (Continued)

increases with each iteration, and where the iterative process continues until a final list of potential match candidates is determined. The system may also comprise a processor configured to receive data indicative of the biometric sample and iteratively engage the comparison model such that results of the first iteration are provided as an input to a second iterator.

20 Claims, 7 Drawing Sheets

(56) References Cited

U.S. PATENT DOCUMENTS

| | | | |
|---|---|---|---|
| 6,047,282 | A | 4/2000 | Wilson et al. |
| 6,070,159 | A | 5/2000 | Wilson et al. |
| 6,240,200 | B1 | 5/2001 | Wendt et al. |
| 6,591,224 | B1 | 7/2003 | Sullivan et al. |
| 6,895,104 | B2 | 5/2005 | Wendt et al. |
| 7,117,356 | B2 | 10/2006 | LaCous |
| 7,155,040 | B2 | 12/2006 | Nikiforov |
| 7,203,343 | B2 | 4/2007 | Manasse et al. |
| 7,359,553 | B1 | 4/2008 | Wendt et al. |
| 7,415,605 | B2 | 8/2008 | LaCous |
| 7,454,624 | B2 | 11/2008 | LaCous |
| 7,502,938 | B2 | 3/2009 | LaCous |
| 7,539,331 | B2 | 5/2009 | Wendt et al. |
| 8,055,027 | B2 | 11/2011 | Nikiforov |
| 8,214,652 | B2 | 7/2012 | LaCous |
| 8,442,967 | B2 | 5/2013 | Brauckmann et al. |
| 2003/0044052 | A1* | 3/2003 | Martin ............... G06K 9/00093 382/125 |
| 2005/0039053 | A1 | 2/2005 | Walia |
| 2005/0160398 | A1* | 7/2005 | Bjornson ............... G06Q 10/06 717/104 |
| 2005/0207626 | A1 | 9/2005 | Kang |
| 2005/0223236 | A1* | 10/2005 | Yamada ............. G06K 9/00006 713/186 |
| 2006/0181521 | A1 | 8/2006 | Perreault et al. |
| 2007/0214365 | A1 | 9/2007 | Cornett et al. |
| 2008/0159598 | A1 | 7/2008 | Iasso |
| 2008/0235233 | A1 | 9/2008 | Holden |
| 2008/0273767 | A1* | 11/2008 | Lo ..................... G06K 9/00087 382/124 |
| 2009/0064303 | A1 | 3/2009 | Dickinson et al. |
| 2009/0174526 | A1* | 7/2009 | Howard ............. G06K 9/00006 340/5.52 |
| 2009/0222212 | A1* | 9/2009 | Curran ................... G06F 19/18 702/19 |
| 2010/0017856 | A1 | 1/2010 | Mercredi et al. |
| 2010/0266168 | A1* | 10/2010 | Wang .................... G06K 9/001 382/124 |
| 2011/0191329 | A1 | 8/2011 | Petrov et al. |
| 2011/0275068 | A1* | 11/2011 | Dear ................... C12Q 1/6851 435/6.11 |
| 2013/0083975 | A1 | 4/2013 | Partington et al. |
| 2013/0086090 | A1 | 4/2013 | Partington et al. |
| 2013/0160144 | A1 | 6/2013 | Mok et al. |
| 2013/0216095 | A1* | 8/2013 | Yabuki ............... H04L 63/0861 382/103 |
| 2013/0246388 | A1 | 9/2013 | Benini |
| 2013/0259330 | A1 | 10/2013 | Russo et al. |

OTHER PUBLICATIONS

International Search Report and Written Opinion for International Application No. PCT/US2014/068978, dated Jan. 5, 2015, date of filing: Oct. 3, 2014, 12 pages.
CN101526880B. English Translation. Jul. 27, 2011.
How Apple's TouchID Fingerprint Sensor Works to Protect Your Identity. Lee, Adriana, 2013.
Sensor Synaesthesia: Touch in motion, and Motion in Touch. Hinckley et al. CHI 2011.
International Search Report and Written Opinion for International Application No. PCT/US2015/019141, dated May 29, 2015, date of filing: Mar. 6, 2015, 16 pages.
International Preliminary Report on Patentability dated Nov. 24, 2016 for Application No. PCT/US2015/024009.
Jain et al., "Score Normalization in Multimodal Biometric Systems", Pattern Recognition, vol. 38, Issue 12, Dec. 2005, 2 pages.
Jain et al,, "Multibiometric Systems", Commun. ACM 47, 1 (Jan. 2004), pp. 34-40.
Maltoni et al., "Handbook of Fingerprint Recognition", Second Edition, Springer, 2009, 506 pages.

* cited by examiner

ADAPTIVE SHORT LISTS AND ACCELERATION OF BIOMETRIC DATABASE SEARCH

CROSS-REFERENCE TO RELATED APPLICATION

The present application claims the priority of U.S. Provisional Application Ser. No. 61/993,643, filed on May 15, 2014, the contents of which is hereby incorporated by reference in its entirety.

BACKGROUND

It is often necessary today to retrieve and compare biometric samples, or other exemplary identification samples, in order to properly identify a person. For example, a DNA test may be run in order to determine a person's genetic history, and/or to identify a potential perpetrator of a crime. Biometric data is often kept for comparison and stored in large databases, potentially with millions of other specimens. For example, in one embodiment, the biometric data could comprise fingerprint scans and the database could be filled with fingerprint scans from all of the customers of a mobile phone company, all of the customers for a banking institution, and/or all arrested felons in a given state. The example of fingerprint information as one of the types of biometric data collected and stored is to be understood as exemplary only. Additionally, biometric data may be used for purposes other than identification, for example a user may need to provide a fingerprint or iris scan in order to complete an authentication process.

Biometric databases are often searched to find a match to a given sample input. The purpose of the search may be to confirm the identity of the source of the sample, or to find a source. One of the most important components of a modern biometric application is the comparison module, which supports recognition functionality. Comparison modules provide one way to numerically estimate the quality of a match of a biometric specimen against one kept in a database. Customarily, the quality of a match is called a comparison score.

Typically, large biometric databases can hold up to hundreds of millions of records. As a consequence, the biometric application and the comparison module need to produce and analyze millions of scores in real time. Unfortunately, this can often result in the process of determining a match requiring a lengthy period of time to complete. Determining a match may also require a significant amount of processor power. A solution to these problems is desired.

SUMMARY

A system for comparing a biometric sample against a biometric dataset is provided. In one embodiment, a system for comparing a biometric sample against a biometric dataset comprises a database storing at least one biometric dataset. The system may also comprise a comparison module configured to iteratively provide a comparison score for each record in the biometric dataset, wherein the comparison score indicates a likelihood of match between an individual record in the biometric dataset and the biometric sample; wherein, during each iteration. The steps in the iteration may comprise retrieving a model of each of the plurality of records. The steps in the iteration may also comprise comparing the model of each of the plurality of records against the biometric sample. The steps in the iteration may also comprise generating the comparison score for each of the plurality of records. The steps in the iteration may also comprise iteratively compare the biometric sample against a plurality of records. The steps in the iteration may also comprise wherein the resolution of the retrieved model increases with each iteration, and where the iterative process continues until a final list of potential match candidates is determined. The system may also comprise a processor configured to receive data indicative of the biometric sample and iteratively engage the comparison model such that results of the first iteration are provided as an input to a second iterator. These and various other features and advantages that characterize the claimed embodiments will become apparent upon reading the following detailed description and upon reviewing the associated drawings.

DETAILED DESCRIPTION

Biometric data can often be stored in large databases. Additionally, a single database may contain a plurality of identification mechanisms. These biometric identification mechanisms may include, for example, fingerprint images, DNA samples, RNA samples, iris scans, or any other mechanism for identifying an individual. Such a database containing biometric data samples may need to be searched against a received inquiry for a match. A database full of biometric data may be searched by a company. For example, a sample may be provided by a customer of that company in order to determine that customer's identity, or to grant access to the account related to that customer.

Figure 1A:
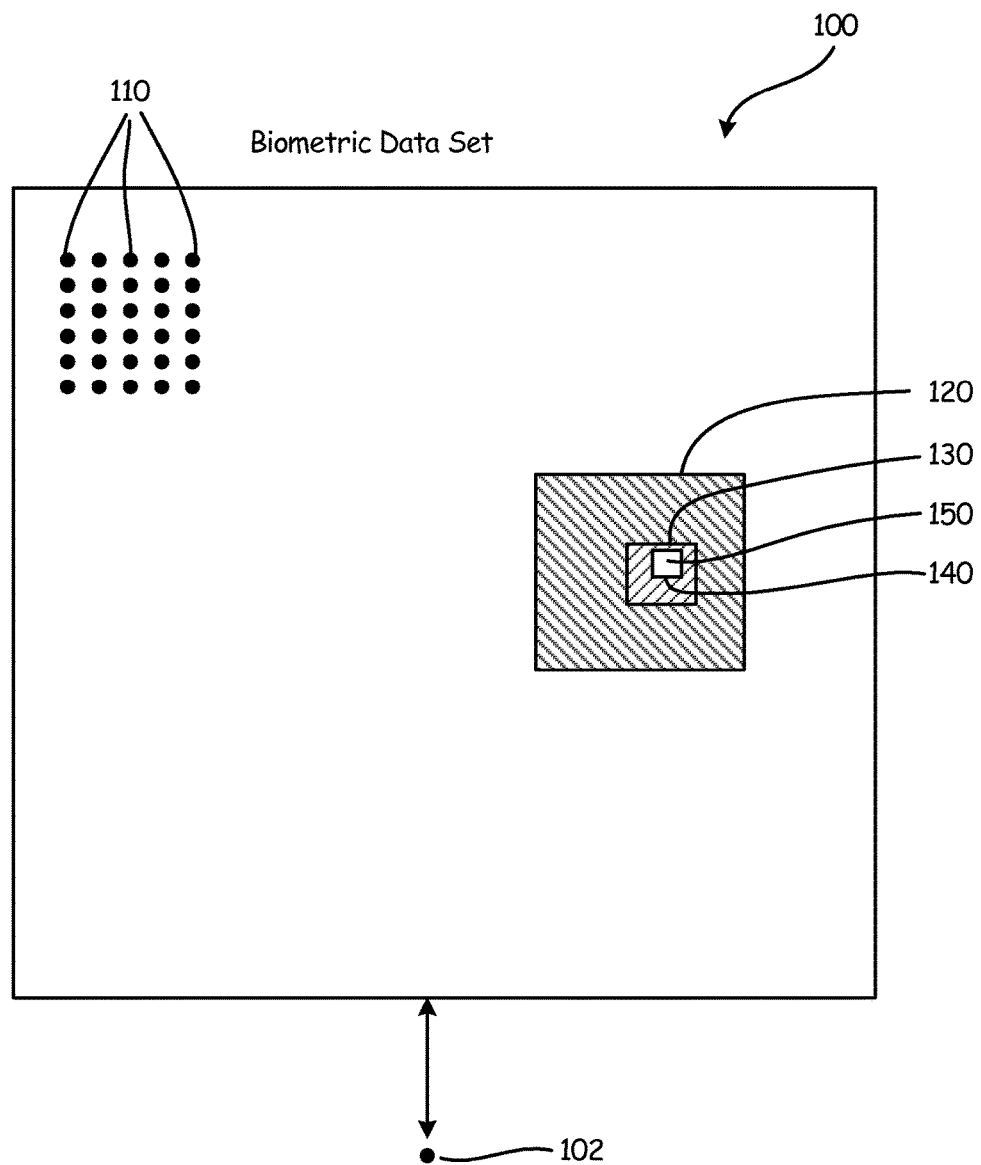
FIG. 1A illustrates an exemplary biometric dataset containing a plurality of records.

FIG. 1A illustrates an exemplary biometric dataset containing a plurality of records. For example, as shown in FIG. 1A, a single database may contain a biometric dataset 100. The biometric dataset 100 may comprise a plurality of biometric data records 110, for example, over one million data records. In another embodiment, the dataset 100 may contain tens or hundreds of millions of data records 110.

Searching dataset 100 may begin by a system receiving a probe 102 as well as instructions to compare the dataset 100 to find an exemplary match 150 to the probe 102. The process of searching biometric dataset 100 for match 150 may require comparing each biometric data sample 110 against probe 102, which may require a significant amount of time and processor power.

Staged Scoring Procedure

In one embodiment, to accelerate the process of finding a match 150 to a received probe 102, a staged scoring procedure is implemented. The procedure utilizes a very fast but less accurate scoring routine to produce a shortlist of possible match candidates, for example, ten percent of the records originally searched. For a search conducted on dataset 100, this may correspond to a first subset 120 as shown in FIG. 1A. The next step in the procedure could be, for example, using a more accurate scoring routine in order to obtain a second subset of results 130, corresponding to a second shortlist. In one embodiment, the second subset of results 130 comprises ten percent of the results returned in the first subset 120, or 1% of the original dataset. This process could continue to return a third subset 140 and continue further until a match 150 is identified. A series of more accurate scoring routines is thus used to repeatedly narrow the number of records until a top scoring match, or several top scoring matches, are reached. In one embodiment, the biometric dataset 100 of FIG. 1A could be narrowed to a series of, for example, five to ten fingerprint samples, of which match 150 is one, the samples then being presented to a user.

In one embodiment, as described above, during each phase of the scoring procedure, 90% of the previous dataset is eliminated, returning a shortlist comprising 10% of the previous dataset. However, in another embodiment, 95% of the previous dataset is eliminated, with 5% returned as a shortlist. In another embodiment, only 80% of the previous dataset is eliminated, with 20% returned as a shortlist. The advantage to returning a larger proportion as the shortlist is that a lower accuracy scoring routine, allowing a given phase of the scoring procedure to proceed more quickly, due to the exponential decrease in remaining records after each round. However, returning a shortlist with fewer results in a given phase may require fewer phases overall. Therefore, in an embodiment with an accuracy factor, A, the number of samples in a shortlist S, from an initial database D, after an nth phase, is dictated by Equation 1, below, where A is the percentage eliminated after each round.

$$S_n = D\left(\frac{100 - A}{100}\right)^n \qquad \text{Equation 1}$$

Additionally, in each phase of the scoring procedure, a different percentage may be eliminated, for example 50% in a first phase, 80% in a second, 90% in a third, and 95% in a fourth, resulting in 0.05% of original samples remaining In another embodiment, at least two phases of the scoring procedure may eliminate the same percentage of data samples. Therefore, in an embodiment with accuracy factors $A_1$-$A_n$, the number of samples left in a shortlist S, from an initial database D, is shown below:

$$S_n = D\prod_{i=1}^{n}\left(\frac{100 - A_i}{100}\right) \qquad \text{Equation 2}$$

Figure 1B:
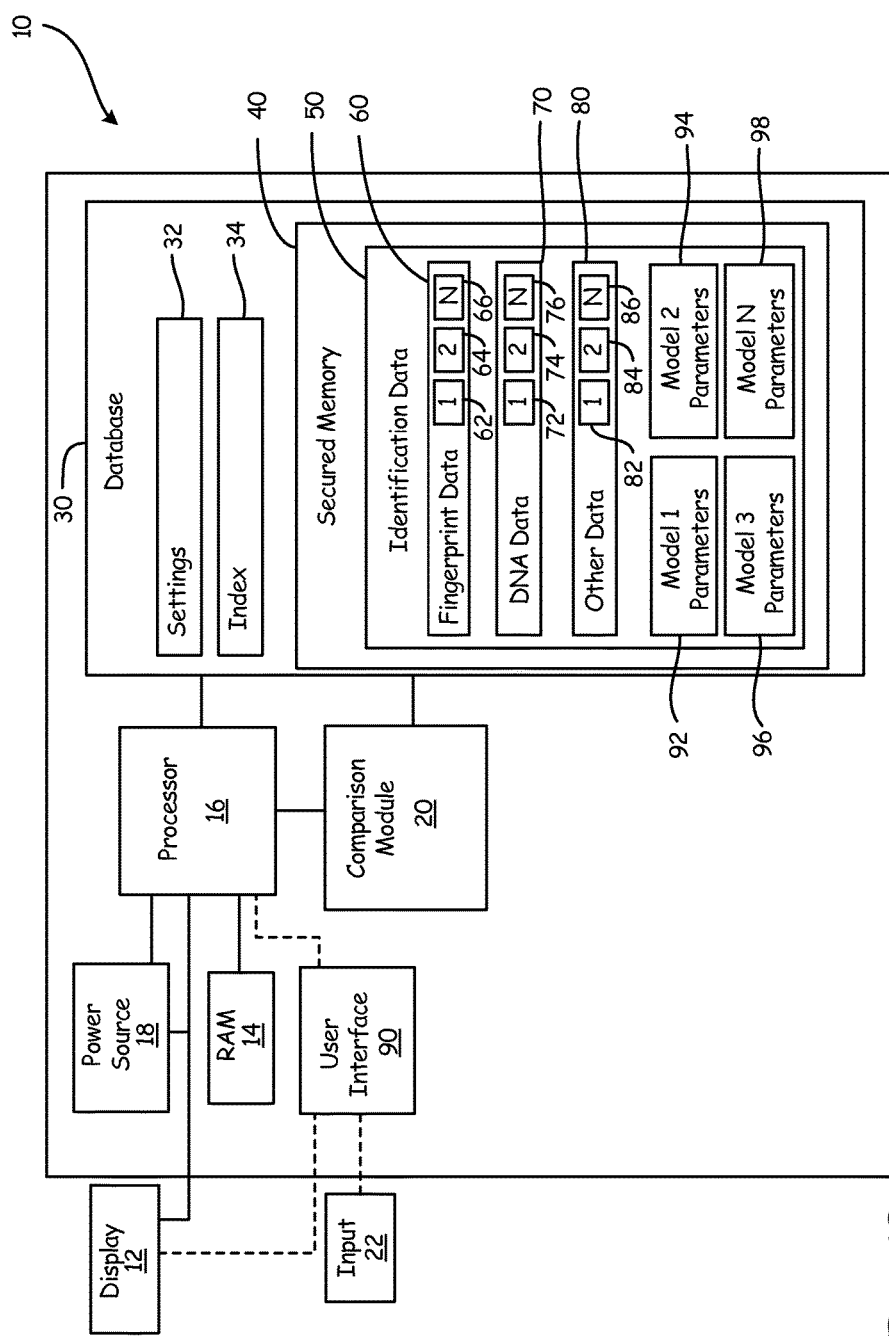
FIG. 1B illustrates an exemplary computer with a comparison module.

FIG. 1B illustrates an exemplary computer with a comparison module. In one embodiment, computer 10, conducts the staged scoring procedure set forth above. Computer 10 may comprise, in one embodiment, a random access memory (RAM) 14 module. In one embodiment, RAM 14 may store information about an ongoing phase of the staged scoring procedure. Computer 10 may also comprise, in one embodiment, a processor 16 which is used by comparison module 20 in determining whether an input sample 22 matches a sample in database 30. In one embodiment, computer 10 also comprises a power source 18. The computer 10 may further comprise, in one embodiment, an external display 12 on which results may be presented to a user. In one embodiment, the user may interact with a user interface 90, either to input a sample through input 22 or to view results in display 12.

In one embodiment, the database 30 comprises an index 34 and saved settings 32. The database may also include, in one embodiment, a secure memory 40 that includes at least a series of identification data 50. In one embodiment, the secure memory 40 cannot be directly accessed by a user, in order to prevent hacking or other misappropriation of the identification data 50.

In one embodiment, the identification data may comprise fingerprint data 60. In another embodiment, identification may comprise DNA data 70. In a further embodiment, identification data may comprise other biometric data 80. In a further embodiment, database 30 may comprise any combination of fingerprint data 60, DNA data 70 or other data 80. Further, while database 30 is shown with a single secure memory 40, it is understood that the methods and systems described herein could apply to a plurality of databases all accessible by the comparison module 20.

In one embodiment, each portion of identification data 50 illustratively includes a plurality of data models. For example, as shown, each portion of fingerprint data 60 stored in the secure memory includes a first model 62, a second model 64, up to and including an nth model 66. In one embodiment, each of these models comprise an increasingly detailed record, with higher resolution. For example, the first model 62 may comprise only a few bits of data describing a fingerprint record 60, while the nth model of fingerprint data 60 may comprise several kilobytes worth of data. For DNA data 70, models 72 through 76 may comprise an increasing number of markers available for comparison. Each of the models may have a corresponding set of parameters that are also stored in the secure memory, for example, model one parameter 92, model two parameter 94, model three parameter 96, up to and including model N parameter 98. In this way, the database can be searched through increasingly specific models in series. In one embodiment, the data models 62 through 66 are generated according to parameters 92 through 98 in response to receipt of a probe 102, and are not stored as separate records in the database 100. In another embodiment, each time database 30 receives a new fingerprint data sample 60, successively details models are accessed and stored separately as different records in database 30.

In an exemplary staged scoring procedure, after a probe 102 comprising a sample fingerprint is received, a first phase in initiated. In the exemplary first phase of a staged scoring procedure, model one dataset 62 is used to create a first shortlist from the dataset 100. In the second phase of the exemplary, model two dataset 64 is used against the first shortlist to generate a second shortlist, where model two dataset comprises higher resolution data than model one dataset. Increasingly detailed datasets are used to generate increasingly reduced shortlists until the nth phase, where the nth model dataset 66 is compared against the (n−1) shortlist, to generate the nth shortlist which, in one embodiment, is the final result set.

The shortlists created during a comparison are typically stored in the RAM 14 in order to reach maximal possible processing speed. In one embodiment, only one shortlist is generated at a time, such that the second shortlist is generated by eliminating non-matching samples from the first shortlist, and such that the third shortlist is generated by eliminating non-matching samples from the second shortlist, and continuing until the nth shortlist is generated.

Figure 2A:
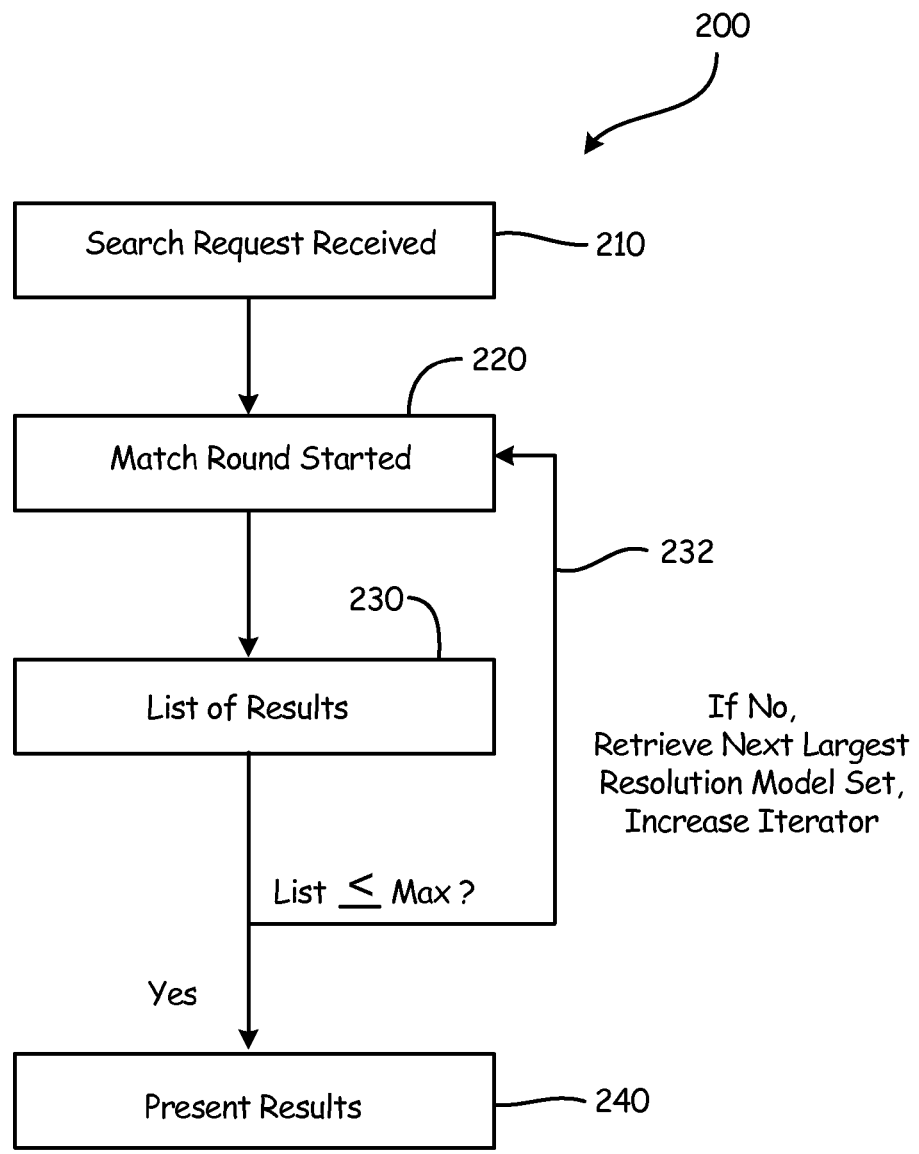
FIG. 2A depicts a method for determining a match based on model data.

FIG. 2A is a flow diagram of a method for determining a match based on model data. FIG. 2A shows an exemplary method 200 for iteratively narrowing a series of samples within a biometric database, for example database 100, in order to determine a match to a received probe, for example probe 102. In one embodiment, method 200 is designed to run as an iterative method.

In one embodiment, the method 200 starts at block 210 wherein an initial search request is received. This may, for example, be a probe provided by a company in one embodiment. It could also, for example, be a fingerprint entered as part of a search of a police database.

In one embodiment, the method 200 then moves to a loop comprising blocks 220 and 230. In block 220, a matching phase is completed and a shortlist is generated based on the scoring procedure described above. In block 230, the list of results is compiled and, in one embodiment, an indication is provided to a user that an iteration has completed. In the first iteration of a staged scoring procedure, the model of the fingerprint comprising the smallest size is used, for example, the first model 62 as shown in FIG. 1B. The smaller model size allows the first scoring run to be completed very quickly, but with less accuracy as the smallest model has the lowest resolution. The output of this first scoring round (in one embodiment, ten percent of the samples input) is then presented as the list of results 230.

In one embodiment, as part of the search request process in block 210, a user can input a desired number of matches, for example a top 10 or a top 100 potential matches. If the list returned in block 230 is greater than the number of the maximum result that a user desires, the process then goes back for another round of matching as shown by arrow 232 back to block 220. When method 200 returns to block 220, in one embodiment an iterator is increased to reflect another iteration has started.

The output of the first scoring round 230 is, in one embodiment, used as the sample set for the second scoring round. The next smallest size model is used for the second scoring round, for example, the second model 64 of fingerprint data, resulting in an increased accuracy with the increase in resolution presented by the increase in model size. In one embodiment, the model size corresponds to an iterator, for example iterator 2 may trigger the use of model dataset 64. The second iteration then allows for an increased amount of time per comparison as the analysis time for each sample increases with the increasing resolution. The output of this second scoring round (in one embodiment ten percent of the samples input, or one percent of the original database) is then used for the sample set for the third scoring round, during which a third model size may be used. The model size increases with each iteration until model size N 66 is used, in the nth iteration.

The use of a staged scoring process, such as that of method 200, increases the efficiency of the comparison module as increased analysis time is only required on smaller and smaller sets of biometric records. In one embodiment, the desired number of samples is a single match. In another embodiment, the desired number of samples remaining is less than five, or less than 10, or less than 25. Once the desired number of results is less than a maximum preset number which, for example, is stored in settings 32 of the database 30, the iterative portion of method 200 ends, and the process moves onto block 240, where the results are presented to a user, or otherwise returned to the requestor of the database comparison.

In one embodiment, samples are added to a shortlist or discarded, in method 200, based on a scoring and sorting procedure, with all but a top percentage of scores (e.g. the top 50% or 10%, or 5%) being discarded. In another embodiment, samples are scored and kept only if their comparison score is above a threshold elimination score.

Figure 2B:
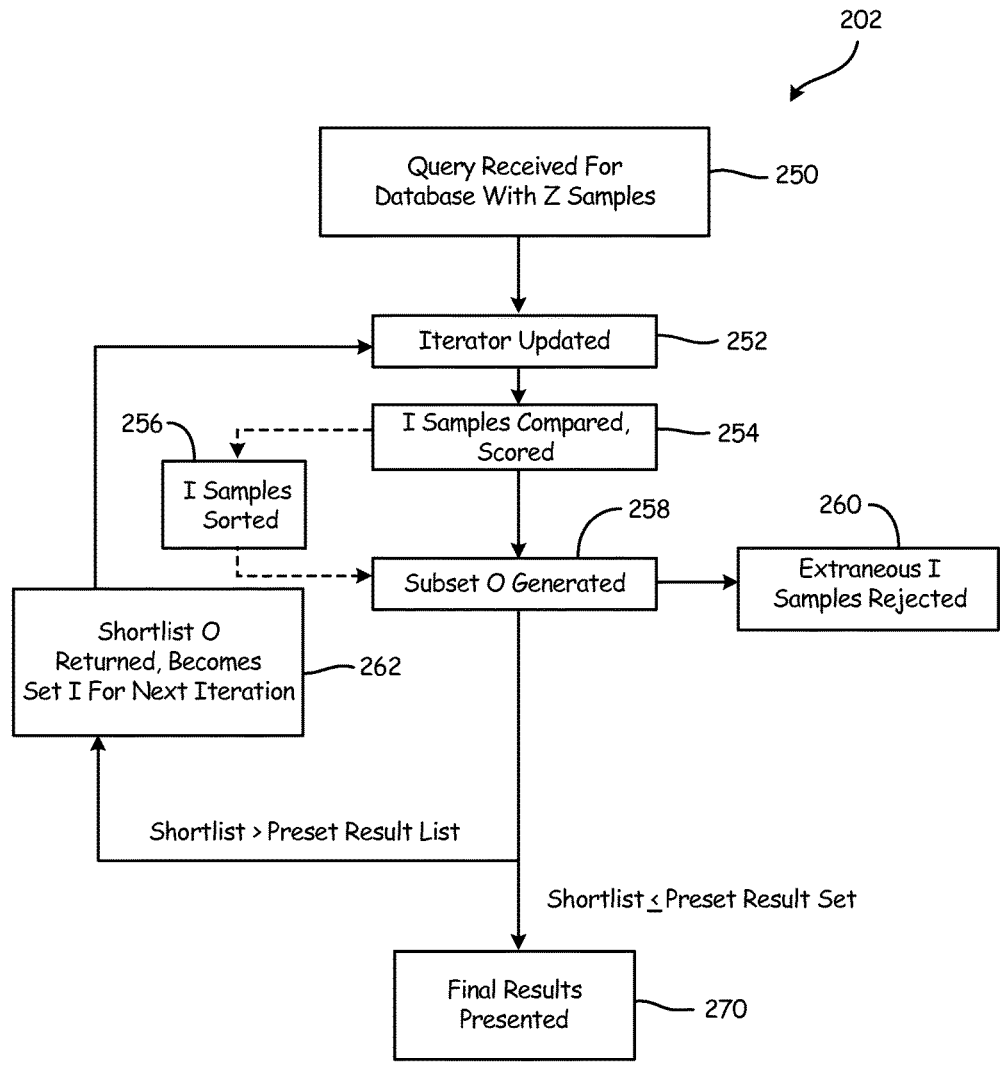
FIG. 2B depicts an iterative method for determining a subset of potential matches.

FIG. 2B is a flow diagram of an iterative method for determining a subset of potential matches in accordance with an embodiment of the present invention. Method 202 involves scoring and optional sorting matches based on comparison scores. Method 202, in one embodiment, includes a scoring process during each iteration. Method 202 starts with a first iteration and continues until an nth iteration results in a final shortlist, which is presented to the requestor of the comparison. In one embodiment, the nth shortlist may comprise a single sample. In another embodiment, the nth shortlist may comprise the top 5 or 10 samples.

Method 202 begins at block 250 where a full database, with sample size Z is presented with a query. Method 202 then starts an iterative process comprising blocks 252, 254, 258, 260, 262 and an optional step 256, as shown in FIG. 2B.

Each iteration starts in block 252 with an iterator updating. In one embodiment, the iterator starts at 1, and increases by 1 each time the method progresses through the loop of blocks 252-262. The iterator, then, corresponds to the shortlist number currently being generated. In one embodiment, each successive shortlist replaces a previous shortlist. In another embodiment, an indication of a sample's presence in a specific shortlist is stored with the data sample, or as part of index 34. In another embodiment, indications of samples present on a current shortlist are only stored in RAM until the iterative process returns a final set of potential matches.

In block 254, a set of I samples is processed, where I corresponds to an input set, which, in one embodiment, is the previously created shortlist. For example, in comparing a probe against a database of 10,000,000 samples, in a first iteration, I corresponds to all 10,000,000 samples of the database. In a second iteration, where the top 10% of samples are kept, I corresponds to the remaining 1,000,000 samples. In a third iteration, I corresponds to the remaining 100,000 samples. The process may continue until, for example, 10 samples are presented to a user as the final result set in block 270. The processing of block 254 may comprise, in one embodiment, comparing a model, corresponding to the iteration number in one embodiment, of each sample of sample set I against a given probe, and assigning a comparison score to each of the samples.

In one embodiment, the scored samples I are sorted, in block 256. This may be necessary, for example, in an embodiment where the scores are obtained on multiple processors. However, in an embodiment where scores are normalized, for example the methods discussed in FIGS. 3A-3B below, such a sorting process is not required.

Figure 2C:
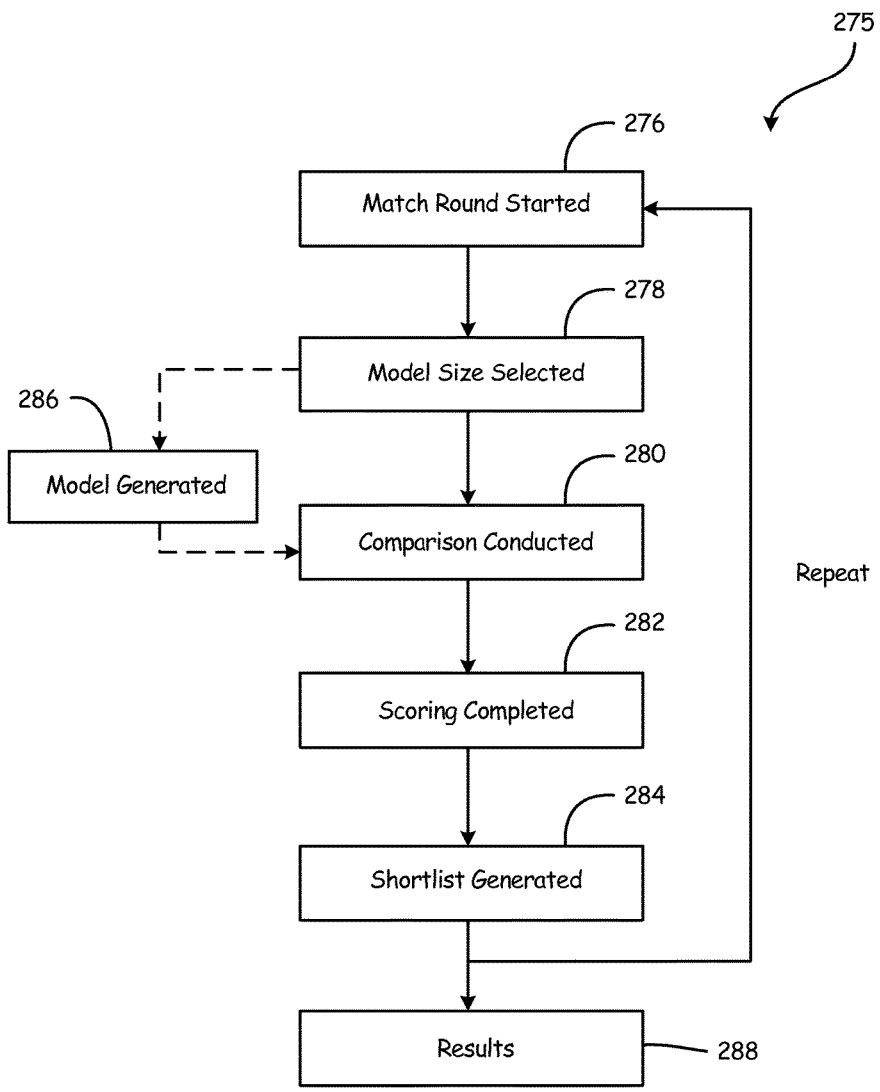
FIG. 2C depicts a method for conducting a match round.

FIG. 2C depicts a method for conducting a match round. In one embodiment, each match round of the process of FIG. 2A or FIG. 2B comprises method 275. Method 275 illustratively starts in block 276, with a match round starting. This may be the first iteration, or a later iteration in a staged scoring procedure.

In one embodiment, the method 275 continues in block 278, with a model being selected. In one embodiment, for each record 102, a series of models is stored within the database 30.

In another embodiment, the model to be used in each iteration is generated based on the number of iterations to be conducted. For example, computing device 10 may determine, based on a database size of 10,000,000 and an accuracy factor of 10% that 6 iterations will need to be conducted in order to return a result set of 10 potential matches. This may determine, in one embodiment, that 6 models of increasing resolution for each given biometric data sample 102 is generated. These models may be generated on-the-fly such that only when a potential match is added to a shortlist is a successive model generated. In another embodiment, a series of models may be generated based on the stored parameters 92-98. The generation of models to be used for a given match round is shown in optional block 286.

Once the model has been selected, a comparison is conducted for each biometric sample, in block 280. After each comparison, a score is assigned to the biometric sample, as shown in block 282. Once all of the biometric samples have been scored, a shortlist is generated in block 284. The shortlist of block 284 may be generated, in one embodiment, in a manner similar to that shown in FIG. 2B. Once the match round is completed, the method either returns to block 276, if another iteration is needed, or the results are presented to the requestor, in block 288, if the current match round was the last iteration.

In one embodiment, subset O, corresponding to the samples output from a given iteration, is generated in block 258. Subset O may be generated, at least in part, based on the scores of sample set I. In one embodiment, subset O is generated by taking a top percentage of scored samples in sample set I. In another embodiment, subset O is generated by taking all samples from sample set I above a given threshold score. Samples from sample set I that do not become part of subset O are discarded in block 260.

In one embodiment, subset O is presented to the user as the current shortlist. In another embodiment, the comparison module automatically converts subset O into the next sample set I, and the next iteration begins, as indicated in block 262. In one embodiment, the subset O is stored in RAM 14 during the iterative process. The method then continues until a final result set is provided to a user in block 270.

Staged Scoring Without Sorting.

One of the problems of using a conventional comparison model, involving sorting and scoring, is that such a method is difficult to run in parallel, because of the need to recombine and sort the scored samples after each iteration. One difficulty of sorting algorithms is that they are not efficient in high parallelization, as, after each iteration, the scores must be compiled across each of the parallel processors to allow for sorting. This limits the efficiency of the comparison model, increasing the time it takes to complete a comparison, or each iterative stage of a comparison, considerably.

Additionally, an inevitable overhead of the conventional approach is the necessity to keep the shortlists sorted. Given the database size of, for example, ten million, in one embodiment, a shortlist may need to keep a sorted list of one million scored samples. This has a negative impact on the identification speed of the biometric application. This lack of efficiency results as, after each stage, the lists created by the different parallel processors must be recombined and sorted before they can be segmented and run again on the parallel processors.

Another important factor in any biometric application is that scores are, in part, random. The reason for this is that biometric specimens may contain at least some noise. This fact makes it much more difficult in choosing a threshold numerical value in order to determine whether a score should be included in a shortlist. Further, in many cases, biometric scores obey a Gaussian distribution. Typical normalization procedure implies computing an average $\alpha$, and standard deviation $\sigma$, and replacing a given comparison score X for a given sample, with $(X-\alpha)/\sigma$. This allows the staged scoring procedure to be run across parallel processors as the need to recombine shortlists after each phase is removed. Instead, the shortlist generated on each parallel processor can be normalized against itself during each stage. This removes the necessary step, in a conventional comparison procedure, of recombining the shortlists of all of the processors in between each iteration of the staged scoring procedure.

Assuming that a score distribution is approximately normal, which is true for at least the first iteration of a staged scoring procedure, and continues to be true as long as the shortlist remains sufficiently large, it may be possible to eliminate the need for sorting during each iteration. A process of scoring without sorting is presented in FIG. 3A, for a biometric database with N samples.

Figure 3A:
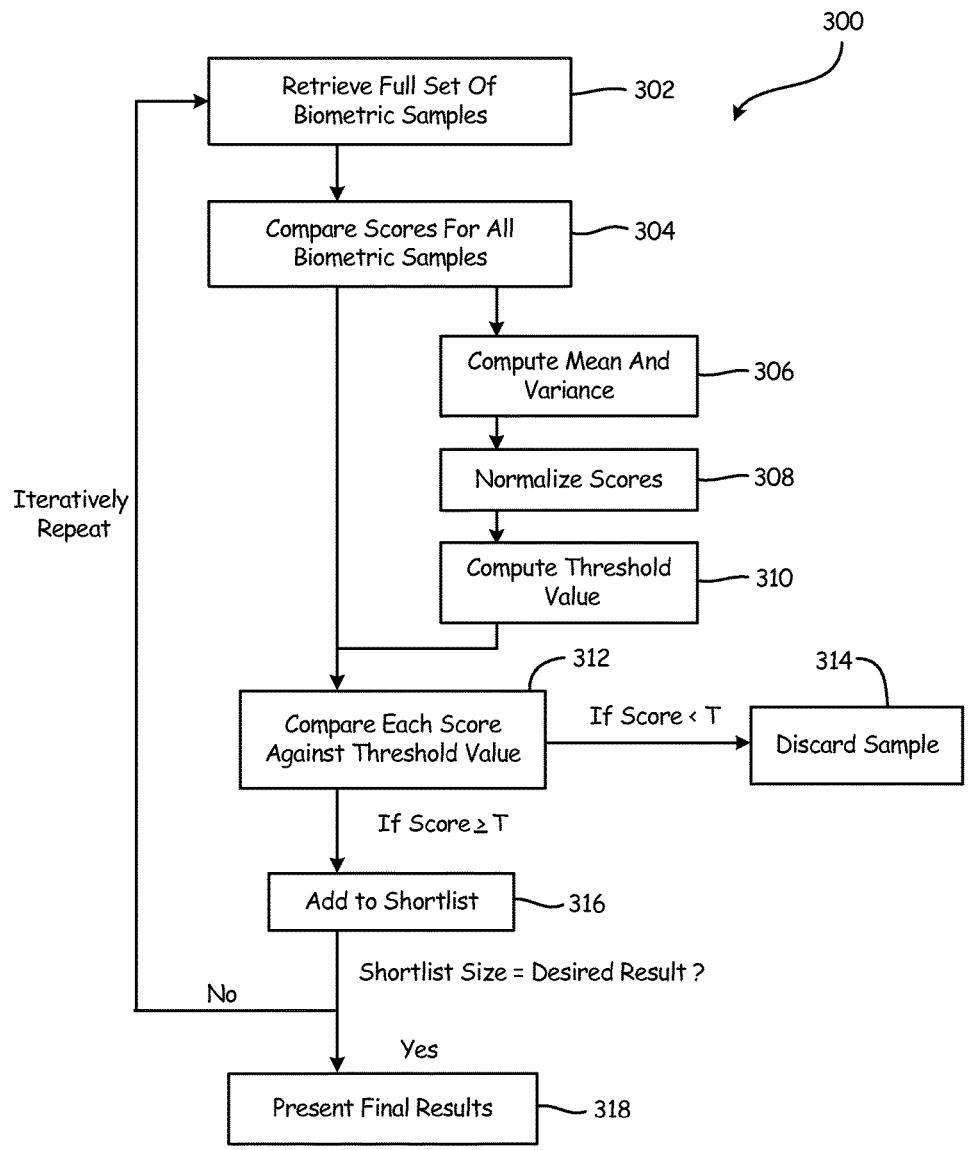
FIG. 3A depicts a method for creating a shortlist of potential matches.

FIG. 3A depicts a method for creating a shortlist of potential matches. In FIG. 3A a method of determining a potential match 300 first starts by retrieving a full set of biometric samples from a database in block 302. The method then moves on to a comparison step in block 304, where all samples from the full database are compared against the probe 102, and scored accordingly. This first step of scoring requires a normalization of scores: each score $X_i$ is replaced with $Y_i=(X_i-\overline{X})/\sigma$, where $\overline{X}$ denotes the score mean value and $\sigma$ is the corresponding standard deviation.

The next step is to compute a threshold value T, according to block 310, that the normalized scores can be compared against in block 312. The threshold value T is computed according to equation 3 below.

$$\int_T^{+\infty} e^{-\frac{u^2}{2}} du = \frac{N_s}{N}.$$ Equation 3

For example, assume that the database consists of N=one million records, and the goal of a first iteration is to have a shortlist of the length $N_s$=100,000. In that case, the right hand side of equation is equal to 0.1. Solving this equation yields T=1.28. Solving Equation 3 can be done by using z-score lookup tables. The value of T obtained in this manner is called the adaptive scoring threshold value.

Once the threshold value has been computed, the method then moves to block 312 where each score in the set of biometric samples is compared against the threshold value. If the score is less than the threshold value, the sample moves to block 314 where it is discarded. If the score for a specific sample is greater than or equal to the threshold value it is added to the shortlist in block 316. In one embodiment, being added to the shortlist comprises remaining on the current list, which becomes the shortlist once all samples with scores below the threshold value are discarded. In another embodiment, a new shortlist is created in each iteration, and all samples with scores above the threshold value are added to the new shortlist.

Once this process has been completed for all of the samples in a given biometric sample set, this size of the newly generated shortlist is then compared to a desired result size. If the shortlist is greater than the desired result size, the method returns to block 302 for another iteration. The iterative process of blocks 302, 304, 306, 308, 310, 312 and 316 is repeated until the shortlist size is the desired result size. In one embodiment, the shortlist size of each successive iteration is always ten percent of that of the previous iteration. So, for the example above, starting with one million records, the first shortlist size is 100,000, the second shortlist size is 10,000 the third shortlist size is 1,000, the forth shortlist size is 100, and the final shortlist size of 10 may be presented to the user as the final result 318. While this example uses 10% as the exemplary accuracy factor, any other appropriate cut-off measure could be used, for example 20%, 5%, 2% or 1%.

Notably, in method 300, the samples do not need to be sorted during the various iterations. The expensive sorting process can now be replaced by an elementary comparison of whether or not the score is above or below a given threshold, T. This enables a user of method 300 to significantly accelerate searching of a biometric database without any impact on accuracy, both by eliminating the time-consuming sorting step, and by the ability to run the process in parallel.

Method 300 may also be applicable to the sample set where a score distribution is not normal. The equation to be used to determine the threshold value T then reads:

$$\int_T^{+\infty} p(u)\,du = \frac{N_s}{N}. \qquad \text{Equation 4}$$

Here p(U) is the empirical probability density for the score distribution. Based on the score statistics, one can calculate lookup tables for threshold values T for a typical range of ratio (Ns/N). In one embodiment, the system automatically detects whether a score distribution fits a normal distribution, for example in block 308 and calculates threshold value T accordingly in block 310.

A significant advantage to method 300 is that it allows a biometric database to be sorted in parallel. In addition to removing the time taken in a traditional module for sorting, this also allows the process to be further shortened because processors may efficiently run the various iterations in parallel.

Figure 3B:
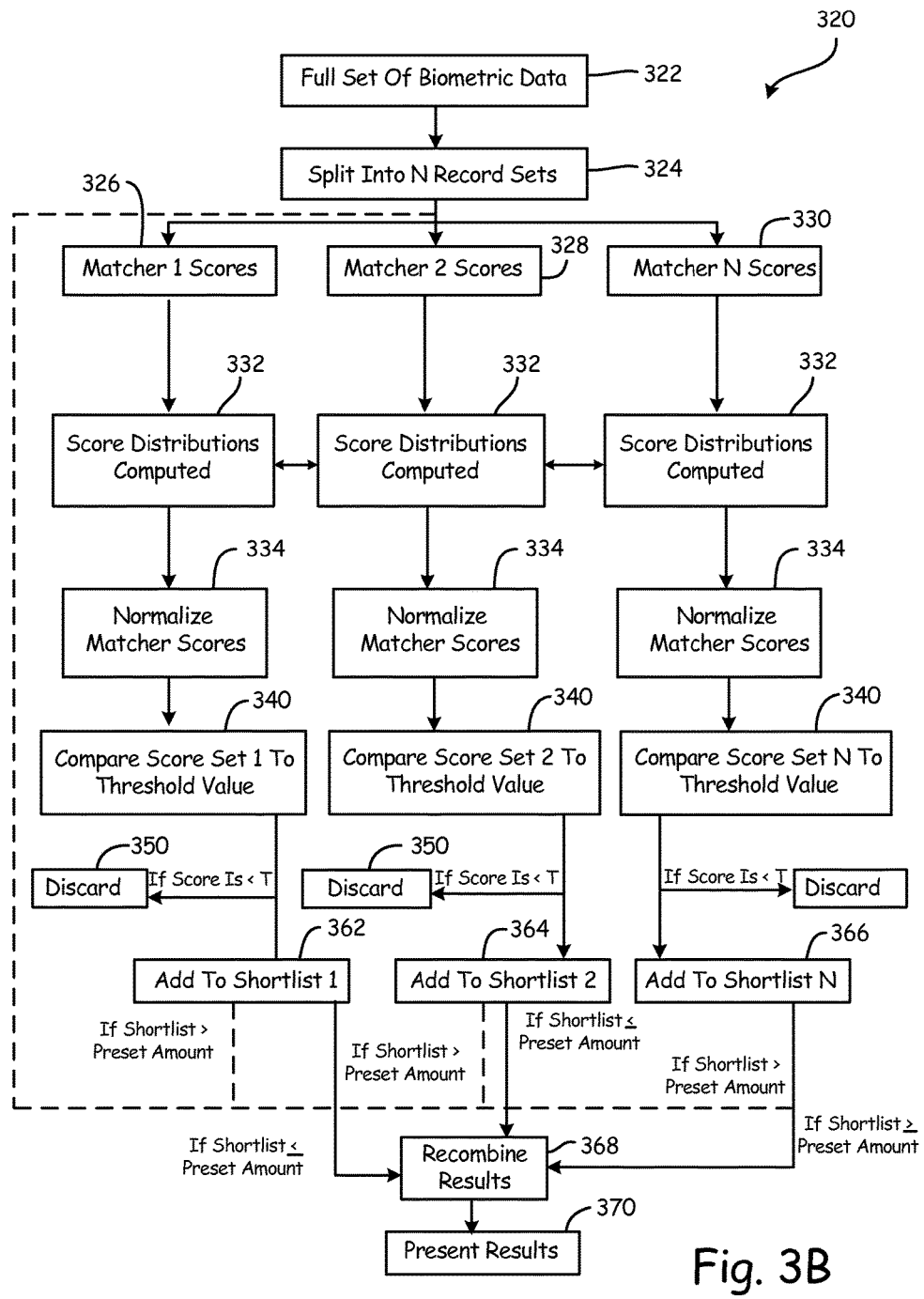
FIG. 3B depicts a method of determining a shortlist by running a series of matchers in parallel.

FIG. 3B depicts a method 320 of determining a shortlist by running a series of matchers in parallel, across processors 1-N. In one embodiment, method 320 runs across two processors. In another embodiment, the method 320 runs across four processors. However, method 320 can be run across any number of processors. In one embodiment, after each iteration, the shortlists of the plurality of matchers 1-N are recombined and redistributed among the matchers 1-N. In another embodiment, as shown in FIG. 3B, the shortlists are not recombined until they are presented to a user as a final list of results.

In one embodiment, the processors running the various matchers in parallel are separate core processors, part of a multi-core processor. In another embodiment, different cores are segmented such that a plurality of matchers run on a single processor core. In another embodiment, a single processor may be segmented into a series of sub processors, each of which may support one of matchers 1-N.

Method 320 starts in block 322 with the full set of biometric data samples, of size Z. The records are then split into a series of N record sets in block 324. Each of these N record sets are then assigned to a matcher, such that matchers 1-N each receive a set of records of roughly the same size. The size of records may be, in one embodiment, determined by evenly distributing the database across the different matchers such that each matcher receives Z/N records.

Block 326 illustrates Matcher1 receiving the first set of records and searching the first set of records for potential matches and assigning a score based on a comparison between each record and a received probe. Matcher2, as shown in block 328, receives a second set of records, which Matcher2 scores against the received probe. In block 330, MatcherN receives an nth set of records, which it scores. In one embodiment, Matcher1-MatcherN conduct their searches simultaneously. In another embodiment, each matcher starts its comparison instantaneously upon receiving its record set, such that a small lag may develop between the Matchers. The process by which each Matcher computes scores for each sample in their record set is similar to that illustrated for a single process in FIG. 3A.

In one embodiment, the scores from all matchers each progress through block 332, where a score distribution is computed. In one embodiment, each Matcher individually computes a score distribution. In another embodiment, the distributions from the different matchers are further computed against each other. At this point, each of the Matchers then normalizes its respective scores, as shown in blocks 334.

Once the scores have been normalized, method 320 moves to blocks 340, where each Matcher compares its record set to the threshold value. In one embodiment, because each matcher scores, normalizes, and computes its threshold value individually, each matcher keeps the same fraction of records from one iteration to another.

Scores that are not equal to or greater than the threshold value T are discarded from a shortlist for each Matcher, as shown in blocks 350. The remaining samples become part of the shortlist for each Matcher, as shown for Matcher1 in block 362, Matcher2 in block 364, and MatcherN in block 366. If, combined, the number of records in each shortlist is smaller than, or equal to, a preset amount, the results are recombined in block 368 and presented to the requesting entity. If the shortlists are greater than a preset final result amount, each shortlist becomes the basis for the next iteration.

Although the present invention has been described with reference to preferred embodiments, workers skilled in the art will recognize that changes may be made in form and detail without departing from the spirit and scope of the invention. For example, while embodiments of the present invention have been described with respect to fingerprints, as fingerprints provide a unique and reliable biometric sample for authentication, one skilled in the art would understand that other biometric data could also be used with the systems and methods described, for example iris patterns, DNA, etc.

What is claimed is:

1. A system for comparing a biometric sample against a biometric dataset, the system comprising:
   a database, storing a biometric dataset, as well as a series of models for the biometric dataset, wherein each of the series of models comprises a different resolution for the biometric dataset;
   a comparison module that iteratively provides a comparison score for each record in the biometric dataset, wherein the comparison score indicates a likelihood of match between an individual record in the biometric dataset and the biometric sample;
   wherein, during each iteration, the comparison model completing a series of steps during each iteration comprising:
   retrieving a model with a resolution of each of the plurality of records;
   comparing the model of each of the plurality of records against the biometric sample;

generating the comparison score for each of the plurality of records;
iteratively compare the biometric sample against a plurality of records; and
wherein the resolution of the retrieved model increases with each iteration, such that, during a second iteration, a second resolution for a second model is higher than a first resolution for a first model, and wherein the results from the first iteration are provided as the input for the second iteration; and
wherein the iterative process continues, with successively fewer results with each iteration, until a final list of potential match candidates is determined, and wherein increasing the resolution with each iteration comprises retrieving a new model with a higher iteration than that used in a previous iteration, and wherein comparing the model of each of the plurality of records occurs in each iteration with the plurality of records left from the previous iteration in an unsorted format; and
a processor configured to receive data indicative of the biometric sample and iteratively engage the comparison model.

2. The system of claim 1, wherein, at the end of each iteration, a shortlist is created of remaining candidates, and wherein each of the shortlists is stored in RAM such that a current shortlist replaces a previous shortlist.

3. The system of claim 1 wherein the model used in a given iteration is generated by the processor at least in part by an indication of iterations needed to get to a size of the final list of potential match candidates.

4. The system of claim 1, wherein the model used in a given iteration is generated by the processor at least in part based on a set of stored parameters.

5. The system of claim 1, and further comprising:
a display configured to display the final list of potential matches.

6. A computer-implemented method for selecting a plurality of potential match candidates from a biometric dataset, the method comprising:
receiving an indication of a biometric sample;
computing a comparison score for each of a plurality of biometric records within the biometric dataset, wherein the comparison score for each of the plurality of records indicates a likelihood of match between each respective biometric record and the biometric sample;
comparing the comparison score for each of the biometric records against a threshold value;
generating a shortlist of potential match candidates to the biometric sample, wherein the shortlist is less than the full set of biometric records;
iteratively repeating the steps of computing the comparison score, comparing the comparison score against a threshold value, and generating the shortlist until the shortlist size is less than or equal to a desired results size;
wherein, for each iteration, the comparison score is computed based on a retrieved model of each of the plurality of biometric records, wherein the retrieved model is one of a plurality of potential models, and wherein, for each iteration, the retrieved model increases in resolution, and wherein the shortlist from the previous iteration is used for the second iteration, such that, for each iteration, a higher resolution model is used on a smaller set of biometric records; and
providing the shortlist as an output once the shortlist size is less than or equal to the desired result size.

7. The computer-implemented method of claim 6, wherein computing the comparison score for each of the plurality of biometric records comprises computing an initial comparison score for each of the plurality of biometric records, calculating a mean, a variance, and a standard deviation for the biometric dataset and normalizing the initial comparison scores for each of the plurality of records.

8. The computer-implemented method of claim 7, wherein, upon detecting a normal distribution of initial comparison scores, the threshold score is calculated based on the normal distribution.

9. The computer-implemented method of claim 7, wherein, upon detecting an abnormal distribution of initial comparison scores, the threshold score is calculated based on the abnormal distribution.

10. The computer-implemented method of claim 6, wherein generating a shortlist of potential candidates comprises discarding a plurality of biometric records with comparison scores lower than the threshold value.

11. The computer-implemented method of claim 6, wherein generating a shortlist of potential candidates comprises adding each biometric record with a comparison score greater than the threshold score to a new shortlist.

12. The computer-implemented method of claim 6, and further comprising:
selecting a model for comparison, wherein the model corresponds to the resolution of each of the biometric records, and wherein the resolution of the selected model increases each time the steps of computing the comparison score, comparing the comparison score against a threshold value, and generating the shortlist are conducted.

13. The computer-implemented method of claim 6, wherein each time the steps of computing the comparison score, comparing the comparison score against a threshold value, and generating the shortlist are conducted, the number of remaining biometric records decreases exponentially.

14. A computer-implemented method for selecting potential match candidates from a biometric dataset, the method comprising:
receiving an indication of a biometric sample;
assigning a plurality of records from the biometric dataset to a plurality of matcher units, wherein each matcher unit is assigned to one of a plurality of processors on the computer;
wherein each matcher iteratively determines a list of potential match candidates for the biometric sample, wherein each iteration comprises the steps of:
computing a comparison score for each of the plurality of records assigned to the matcher, wherein the comparison score is computed by retrieving an iteration model for each of the plurality of records, wherein the iteration model is selected from a set of potential models, each potential module having a different resolution, and wherein each potential model corresponds to each of the plurality of records; and wherein the iteration module is selected such that a second iteration model is a higher resolution than a first iteration model, wherein the second iteration comprises a second plurality of records, received as a result from the first iteration, the second plurality of records comprising fewer records than the plurality of records;
comparing the comparison score for each of the plurality of records against a threshold score; and generating a shortlist of potential match candidates to the biometric sample, wherein the shortlist is less than the full set of biometric records assigned to the matcher.

15. The computer-implemented method of claim 14, wherein each of the plurality of processors on a computing device comprises a subprocessor.

16. The computer-implemented method of claim 14, wherein computing the comparison score for each of the plurality of biometric records comprises computing an initial comparison scores for each of the plurality of biometric records, calculating a mean, a variance, and a standard deviation for the biometric dataset and normalizing the initial comparison scores for each of the plurality of records.

17. The computer-implemented method of claim 16, wherein each matcher is further configured to detect distribution type of initial comparison scores and calculate a threshold score, and wherein the distribution type is detected as either normal or abnormal.

18. The computer-implemented method of claim 14, wherein generating a shortlist of potential candidates comprises discarding a plurality of biometric records with comparison scores lower than the threshold value.

19. The computer-implemented method of claim 14, wherein generating a shortlist of potential candidates comprises adding each biometric record with a comparison score greater than the threshold score to a new shortlist.

20. The computer-implemented method of claim 14, and further comprising:.
   selecting a model for comparison, wherein the model corresponds to the resolution of each of the biometric records, and wherein the resolution of the selected model increases each time the steps of computing the comparison score, comparing the comparison score against a threshold value, and generating the shortlist are conducted.

\* \* \* \* \*